June 10, 1975 W. A. WARRINER Plant Pat. 3,728
ROSE PLANT
Filed March 15, 1974
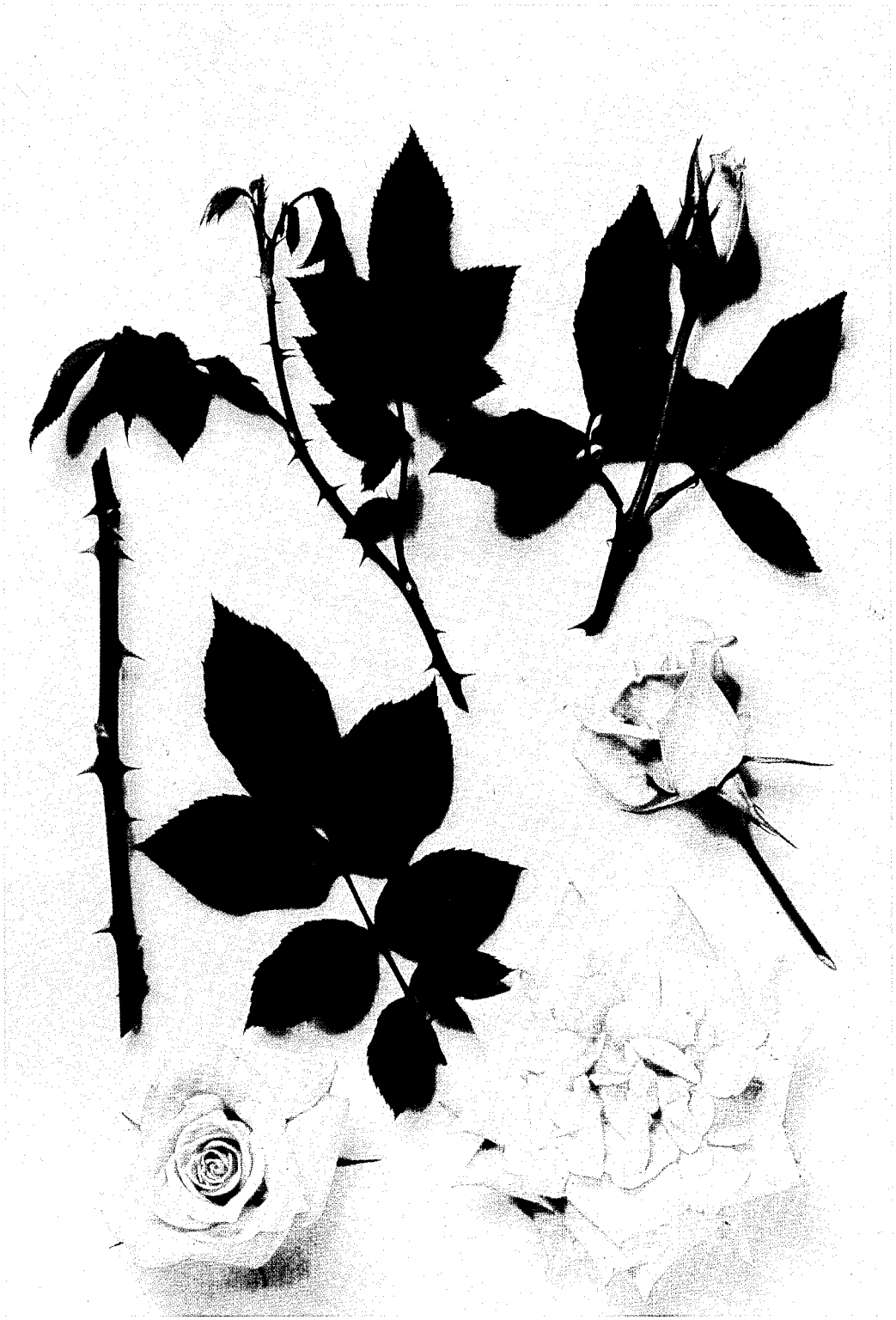

United States Patent

Plant Pat. 3,728

Patented June 10, 1975

1

3,728

ROSE PLANT

William A. Warriner, Tustin, Calif., assignor to Jackson & Perkins Company, Medford, Oreg.

Filed Mar. 15, 1974, Ser. No. 451,499

Int. Cl. A01h 5/00

U.S. Cl. Plt.—26 1 Claim

This present invention relates to a new and distinct cultivar of rose plant of the floribunda class, which was originated by me by crossing the cultivar Bridal Pink, U.S. Plant Pat. #2,851 with pollen from the cultivar Forever Yours, U.S. Plant Pat. #2,443.

One of the main objectives of this breeding was to produce a floribunda cultivar of rose similar in growth to the parent Bridal Pink but with a deeper shade of pink color in the bloom. This objective was achieved, along with other desirable improvements, as evidenced by the following unique combination of characteristics which are outstanding in the new cultivar and which distinguish it from its parents, as well as from all other cultivars:

1. A close similarity in plant habit, foliage thorns, and flower form and size to the cultivar Bridal Pink, U.S. Plant Pat. #2,851.

2. The cultivar has a distinctly different flower color in all stages of development, particularly in the full open stage with a Camellia Rose (Wilson) color compared to the much lighter Eosine Pink (Ridgway) of Bridal Pink.

Asexual reproduction of this new cultivar by budding was performed at Wasco, Calif., and shows that the characteristics and distinctions in this description come true to form and are established and transmitted through succeeding propagations.

The accompanying illustration shows typical specimens of the vegetative growth and flowers of the new cultivar in different stages of development and depicted in color as nearly true as it is reasonably possible to make the same in a color illustration of this character.

The following is a detailed description of the new rose cultivar, with color terminology in accordance with Wilson's Horticultural Colour Chart (W) or Ridgway's Color Standards and Nomenclature (R), except where ordinary dictionary significance of color is indicated.

Parentage: Seedling.

*Seed parent.*—Bridal Pink, Plant Pat. #2,851.

*Pollen parent.*—Forever Yours, Plant Pat. #2,443.

Classification:

*Botanic.*—Rosa hybrid.

*Commercial.*—Floribunda.

FLOWER

Observations were made at Irvine, Calif. in early January 1974, from plants grown in greenhouse.

Blooming habit: Recurrent: continuous.

Bud:

*Size.*—1.25 to 1.5 inches when petals start to unfurl.

*Form.*—Pointed, ovoid.

*Color.*—When sepals first divide, near Geranium Lake 20/1 (W) on outer edges of petals, lightens to Geranium Lake 20/3 (W) toward center of petal, center base of petal being nearly white. When half blown; inside of petals Camellia Rose 622/1 (W); reverse of petals near Neyron Rose 623/1 (W).

*Sepals.*—Color: Outer surface, Scheeles Green 860/2 (W); has many small stipitate glands; Inner surface, Scheels Green 860/2 (W); very little white tomentum. Three appendaged sepals lightly appendaged. Two unappendaged sepals slightly hairy edged.

*Receptacle.*—Color: Scheeles Green 860/2 (W).

2

Shape: Funnel. Size: Large, broad. Surface: Smooth.

*Peduncle.*—Length: Medium. Surface: Slightly prickly. Color: Scheeles Green 860/2 (W). Strength: Stiff, erect.

*Opening.*—Spiral type, outer petals slightly pointed.

Bloom:

*Size.*—Medium. Average size when fully expanded 1.25 to 1.5 inches.

*Borne.*—Singly, occasionally several together.

*Stems.*—Long and medium; strong.

*Form.*—When first open, high center. Permanence—outer petal edges slightly curled.

*Petalage.*—Number of petals under normal conditions 30–35.

*Color.*—Center of flower: Upper side of petals—Camellia Rose 622/1 (W); reverse side of petals—gradation from center base of petal to outer edge of Neyron Rose 623/3 to 623 (W). Outer petals: Upper side of petals, same as center. Reverse of petals, same as center. Base of petals, nearly white with small area near Empire Yellow 603/3 (W). General tonality from a distance Neyron Rose 623/1 (W) when viewed so as to see lower side of petals. Camellia Rose 622/1 (W) when viewed from above. Variegations: veins are darker.

*Discolorations.*—General tonality at end of first day—no changes; third day, slightly lighter than Camellia Rose 622/1 (W), near 622/2 (W).

*Fragrance.*—Slight.

*Petals.*—Thick.

*Surface.*—Inside—satiny; reverse—satiny.

*Shape.*—Round.

*Form.*—Edges slightly quilled.

*Arrangement.*—Imbricated.

*Petaloids in center.*—Few.

*Persistence.*—Drop off cleanly.

*Lastingness.*—On the plant—long. As cut flower—long.

Reproductive parts:

*Anthers.*—Medium. Color—yellow. Arrangement—regular around styles.

*Filaments (threads).*—Long and medium. Color—white.

*Pollen.*—Lemon yellow.

*Styles.*—Bunches, loosely separated of uneven lengths. Color—Carmine 21 (W).

*Stigmas.*—Color—white.

*Ovaries.*—All enclosed in calyx.

Fruit: (Not observed).

PLANT

Form: Bush.

Growth: Very vigorous.

Foliage: Number of leaflets on normal mid-stem leaves, mostly seven, sometimes five.

*Size.*—Very large.

*Quantity.*—Abundant.

*Color.*—New foliage: Upper side—Fern Green 0862 (W) overlaid and edged with Garnet Brown 00918/3 (W); Lower side—mostly lighter than Garnet Brown 00918/3 (W). Old foliage: Near but darker than Parsley Green 00962 (W).

Leaflets:

*Shape.*—Oval pointed.

*Texture.*—Leathery on upper side; smooth on under side. Ribs and veins—ordinary.

*Edge.*—Serrated, undulated.

*Serration.*—Single, small.

*Petiole.*—Rachis—Color—Red on upper side; green below. Underside—prickles.

*Stipules.*—Long, serrated.

*Disease resistance.*—Resistant to mildew under normal growing conditions at Irvine, Calif.

Wood:

*New wood.*—Color—dark green.

*Bark.*—Smooth.

*Old wood.*—Color—green.

*Bark.*—Smooth.

Prickles:

*Quantity.*—On main stalks from base—ordinary. On laterals from stalk—ordinary.

*Form.*—Broad base; hooked downward.

*Color when young.*—Red.

*Position.*—Irregular.

Small prickles:

*Quantity.*—Few on main stalks; few on laterals.

*Color.*—Brown.

I claim:

1. A new and distinct cultivar of rose plant of the floribunda class, substantially as herein shown and described, characterized particularly as to novelty by the unique combination of vigorous habit of growth, high production of cut flowers throughout the year, strong stems suitable for cut flowers, all characteristics which are similar to the cultivar Bridal Pink. The bud and flower color are distinctive and novel in this new cultivar, being near Geranium Lake as the sepals unfold and Camellia Rose in the opening and full open flower.

No references cited.

ROBERT E. BAGWILL, Primary Examiner